(12) United States Patent
Sato et al.

(10) Patent No.: US 7,811,601 B2
(45) Date of Patent: Oct. 12, 2010

(54) OPHTHALMIC LENSES CAPABLE OF SUSTAINED DRUG RELEASE AND PRESERVATIVE SOLUTIONS THEREFOR

(75) Inventors: Takao Sato, Tokyo (JP); Rei Uchida, Tokyo (JP); Kenji Uno, Tokyo (JP)

(73) Assignee: Seed Co., Ltd., Tokyo (JP)

( * ) Notice: Subject to any disclaimer, the term of this patent is extended or adjusted under 35 U.S.C. 154(b) by 917 days.

(21) Appl. No.: 10/549,590

(22) PCT Filed: Mar. 25, 2004

(86) PCT No.: PCT/JP2004/004156
§ 371 (c)(1),
(2), (4) Date: Sep. 20, 2005

(87) PCT Pub. No.: WO2004/090613
PCT Pub. Date: Oct. 21, 2004

(65) Prior Publication Data
US 2006/0187410 A1    Aug. 24, 2006

(30) Foreign Application Priority Data

| Apr. 3, 2003 | (JP) | ............... 2003-100236 |
| Apr. 3, 2003 | (JP) | ............... 2003-100237 |
| Apr. 3, 2003 | (JP) | ............... 2003-100238 |
| Mar. 22, 2004 | (JP) | ............... 2004-082801 |

(51) Int. Cl.
| A61K 9/00 | (2006.01) |
| A61K 9/14 | (2006.01) |
| G02B 1/04 | (2006.01) |
| C08F 30/02 | (2006.01) |
| C08F 130/02 | (2006.01) |
| C08F 230/02 | (2006.01) |
| C08F 12/28 | (2006.01) |
| C08F 20/52 | (2006.01) |
| C08F 20/70 | (2006.01) |
| C08F 22/40 | (2006.01) |
| C08F 120/52 | (2006.01) |
| C08F 120/70 | (2006.01) |
| C08F 122/40 | (2006.01) |
| C08F 220/52 | (2006.01) |
| C08F 222/40 | (2006.01) |

(52) U.S. Cl. ............... 424/429; 424/486; 424/487; 523/106; 526/274; 526/310

(58) Field of Classification Search .................. None
See application file for complete search history.

(56) References Cited

U.S. PATENT DOCUMENTS

| 3,220,960 A * | 11/1965 | Lim et al. ............... 521/149 |
| 4,604,425 A * | 8/1986 | Ohmura et al. ............... 525/88 |
| 4,931,279 A | 6/1990 | Bawa et al. ............... 424/427 |
| 4,983,386 A * | 1/1991 | Kamishita et al. ........ 514/772.1 |
| 5,182,258 A * | 1/1993 | Chiou ............... 514/3 |
| 5,270,415 A * | 12/1993 | Sulc et al. ............... 526/265 |
| 5,520,910 A | 5/1996 | Hashimoto et al. |
| 5,945,121 A * | 8/1999 | Kato et al. ............... 424/450 |
| 6,310,116 B1 * | 10/2001 | Yasuda et al. ............... 523/106 |
| 6,410,045 B1 * | 6/2002 | Schultz et al. ............... 424/429 |
| 6,503,955 B1 * | 1/2003 | Dobrozsi et al. ......... 514/772.4 |
| 6,534,687 B2 * | 3/2003 | Schultz et al. ............... 570/152 |
| 6,589,922 B1 * | 7/2003 | Dow et al. ............... 510/130 |
| 6,713,080 B1 * | 3/2004 | Aiache et al. ............... 424/427 |
| 2002/0071789 A1 | 6/2002 | Molock et al. ............... 422/112 |

(Continued)

FOREIGN PATENT DOCUMENTS

EP          32443 A2 *  7/1981

(Continued)

OTHER PUBLICATIONS

Nakamae et al. Swelling behavior of hydrogels containing phosphate groups. Makromolekulare Chemie-Macromolecular Chemistry and Physics 1992 193:983-990.*

(Continued)

*Primary Examiner*—Robert A Wax
*Assistant Examiner*—Caralynne Helm
(74) *Attorney, Agent, or Firm*—Frommer Lawrence & Haug LLP; Ronald R. Santucci

(57) ABSTRACT

An object of the present invention is to provide a practical ophthalmic lens which has an effect of effectively retaining and sustainedly releasing a drug and has form stability before and after release of the drug, wherein the ionic polymer gel having sustained drug releasability can regulate the amount of the drug included therein, depending on the efficacy of the drug used, and storing solution for a practical ophthalmic lens.

The present invention relates to a drug delivery ophthalmic lens comprising a cationic group-containing drug in the inside of a copolymer consisting of a hydrophilic monomer having a hydroxyl group in its molecule, at least one member selected from specific phosphate group-containing methacrylates a monomer having a nitrogen atom in its side chain, and a monomer copolymerizable with these components, and also relates to a drug delivery ophthalmic lens comprising an anionic group-containing drug in the inside of a copolymer consisting of a hydrophilic monomer, cationic and anionic monomers, and a monomer copolymerizable with these components, wherein the copolymer contains the anionic monomer in a ratio of 30 to 90 mol % to the cationic monomer, and also relates to storing solution for a practical ophthalmic lens.

9 Claims, 2 Drawing Sheets

U.S. PATENT DOCUMENTS

| | | | |
|---|---|---|---|
| 2002/0164379 A1* | 11/2002 | Nishihara et al. | 424/600 |
| 2002/0197300 A1 | 12/2002 | Schultz et al. | 424/429 |

FOREIGN PATENT DOCUMENTS

| | | |
|---|---|---|
| EP | 0 292 909 A2 | 11/1988 |
| EP | 0 595 226 A2 | 5/1994 |
| GB | 1 540 097 | 2/1979 |
| JP | 52-32971 B | 8/1977 |
| JP | 6-9725 A | 1/1994 |
| JP | 6-145456 A | 5/1994 |
| JP | 6-306250 A | 11/1994 |
| JP | 10-197831 A | 7/1998 |
| JP | 11-52303 A | 2/1999 |
| JP | 2003-84248 A | 3/2003 |
| JP | 2003301014 | 10/2003 |

OTHER PUBLICATIONS

Andersson et al. Contact Dermatitis 1999 41:254-259.*
Lee et al. Materials Science and Engineering C 2002 20:161-166.*
Rei Uchida, Azulene Incorporation and Release by Hydrogel Containing Methacrylamide Propyltrimenthylammonium Chloride, and its Application to Soft Contact Lens, Journal of Controlled Release, Elsevier, Amsterdam, NL vol. 92, No. 3, Oct. 30, 2003, pp. 259-264.

* cited by examiner

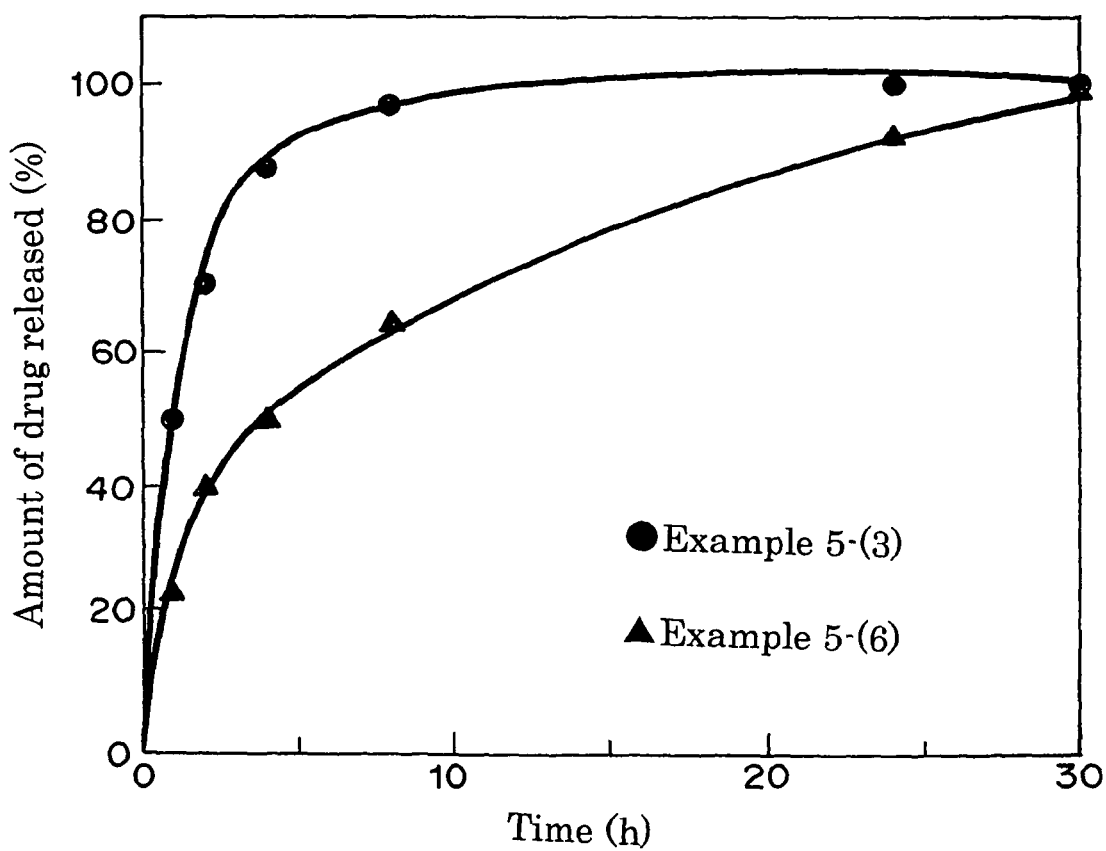

OPHTHALMIC LENSES CAPABLE OF SUSTAINED DRUG RELEASE AND PRESERVATIVE SOLUTIONS THEREFOR

This application is a 371 of PCT/JP2004/004156 filed on Mar. 25, 2004, published on Oct. 21, 2004 under publication number WO 2004/090613 A1 which claims priority benefits from Japanese Patent Application Number 2003-100236 filed Apr. 3, 2003 and Japanese Patent Application Number 2003-100237 filed Apr. 3, 2003 and Japanese Patent Application Number 2003-100238 filed Apr. 3, 2003 and Japanese Patent Application Number 2004-082801 filed Mar. 22, 2004.

FIELD OF THE INVENTION

The present invention relates to a drug delivery ophthalmic lens and a storing solution used therefor. More specifically, the present invention relates to a drug delivery ophthalmic lens used as a contact lens or an intraocular lens consisting of a polymer gel having an ability to include a suitable amount of a drug and to release the drug sustainedly with less change in size upon sustained drug release, as well as a storing solution used therefor.

DESCRIPTION OF THE PRIOR ART

Generally, pharmaceutical preparations administered topically into the front part of the eye include eye drops, a suspension and an ophthalmic ointment, which are different in properties from one another. Administration of eye drops is relatively easy, but after application, eye drops are diluted rapidly with tears and discharged through a lachrymal duct. That is, the time of contacting eye drops with a horny coat should be sufficiently long in order to administer the drug sufficiently. A suspension and an ophthalmic ointment, on the other hand, are superior to eye drops in prolongation of the time of contacting with a horny coat, but suffer from drawbacks such as eye irritation and cloudy views.

As drug release system (DDS) technology utilizing a drug in the ophthalmic region, a polymer gel having a property of sustainedly releasing a drug, prepared by grafting a monomer having an electrolyzable group or a polar group onto polyvinyl alcohol in a hydrated state by irradiation with actinic rays and then impregnating the resulting hydrous gel with a working substance, is disclosed (see, for example, JP-B 52-32971). This prior art polymer gel sustainedly releases its included drug efficiently by the grafted electrolyzable group or polar group, in addition to regulation by its network structure. The electrolyzable group or polar group includes groups in a salt form, for example anionic functional groups such as a carboxyl group, sulfonate group and phosphate group, as well as a quaternary ammonium base.

Further, techniques for strongly retaining an anionic group-containing drug in the inside of an ophthalmic lens and efficiently exhibiting an effect of sustained release are disclosed (see, for example, JP-A 6-145456 and JP-A 6-306250). These techniques involve synthesizing a polymer gel having a cationic group such as a quaternary ammonium salt in its side chain, to coordinate the anionic group-containing drug with the substituent group by ion exchange. The drug coordinated by ion exchange is sustainedly released by ion-exchange reaction in a sustained-release environment.

However, a method of introducing a functional group into a polymer gel, described in JP-B 52-32971 supra, needs a special facility for gamma rays, and is thus problematic in respect of general-purpose properties and utility. To obtain a network structure of the ophthalmic lens practically necessary for form stability etc., the amount of gamma rays applied should be regulated, and when the amount of the rays applied is too high, the ophthalmic lens forms a network structure completely, and suffers from failure to exhibit interaction between the polar group and the working substance, thus failing to attain effective drug releasability.

In JP-A 6-145456 and JP-A 6-306250 supra, on the other hand, the ion exchange reaction between a cationic group as a drug-carrying site and an anionic group in a drug is utilized, so when a drug having a sterically large structure is used, its diffusion into the lens is inhibited to reduce the degree of ion exchange very significantly. Further, the ophthalmic lens has an ionic group in it, thus reacts very sensitively to a change in temperature, pH etc. in an external environment, and hardly attains form stability essential as the ophthalmic lens. That is, there is the problem that the ability of the ophthalmic lens to correct eyesight is hardly stably exhibited. Further, the properties of the cationic group are different before and after sustained release of the drug, thus influencing physical properties of the lens, such as form stability etc.

The cationic groups of the lens having a drug included therein are stabilized in such a state that their charge is cancelled by anionic groups of the drug, and thus electrical repulsion among the cationic groups is not generated, to permit the polymer gel to be shrunk. Upon exposure of the polymer gel once to the physiological environment, however, the drug included therein is released by ion-exchange reaction, and cationic side chains in the polymer gel are strongly charged to generate electrical repulsion to cause the polymer to be swollen. Because of this significant change in the shape of the polymer gel before and after release of the drug, there arise problems such as failure to attain a stable ability to correct eyesight when the gel is used as an ophthalmic lens.

Only about 60% of the functional groups in the polymer gel in JP-B 52-32971, JP-A 6-145456 and JP-A 6-306250 supra participate in inclusion of the drug, so the drug is hardly included in an amount corresponding to the amount of functional groups introduced. Accordingly, the correlation between the content of the drug and the amount of the drug to be sustainedly released cannot be attained at the time of design, and therefore the polymer gel is not practical. From these problems, there is no example on practical use of DDS using a contact lens.

An object of the present invention is to provide a practical ophthalmic lens which has an effect of effectively retaining and sustainedly releasing a drug and has form stability before and after release of the drug in an ionic polymer gel having an effect of sustainedly releasing a drug by ion-exchange reaction, wherein the ionic polymer gel having sustained drug releasability can regulate the amount of the drug included therein, depending on the efficacy of the drug used.

When an ionic component-containing storing solution is used for the drug delivery SCL using ion-exchange reaction according to the present invention, drug ions captured by the ligand are exchanged with ions in the storing solution to allow the drug to be undesirably rapidly eluted. The generally used storing solution contains ionic substances as a buffering agent and an osmotic pressure regulating agent, and can thus not be used as a storing solution for the drug delivery SCL in this case.

Another object of the present invention is to provide a drug delivery SCL storing solution using ion-exchange reaction, particularly a storing solution capable of suppressing elution of a drug included, maintaining the shape of the lens itself during storage, and allowing the lens to be worn as such from the storing solution onto the eyes.

SUMMARY OF THE INVENTION

The present invention relates to a drug delivery ophthalmic lens comprising a cationic group-containing drug in the inside of a copolymer consisting of a hydrophilic monomer having a hydroxyl group in its molecule, at least one member selected from phosphate group-containing methacrylates represented by the following structural formula (I), a monomer having a nitrogen atom in its side chain, and a monomer copolymerizable with these components:

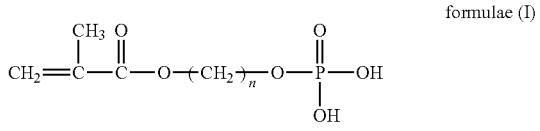

formulae (I)

n: 1~4

The present invention also relates to a drug delivery ophthalmic lens comprising an anionic group-containing drug in the inside of a copolymer consisting of a hydrophilic monomer, cationic and anionic monomers, and a monomer copolymerizable with these components, wherein the copolymer contains the anionic monomer in a ratio of 30 to 90 mol % to the cationic monomer.

Further, the present invention relates to a solution for storing the drug delivery ophthalmic lens, which comprises a nonionic surfactant and a nonionic osmotic pressure regulating agent and is free of an ionic compound.

According to the present invention, there can be obtained a drug delivery ophthalmic lens excellent in strength with less change in size and capable of highly including and sustainedly releasing a drug by utilizing ion-exchange reaction and intermolecular interaction.

The storing solution of the present invention can, without eluting a drug included in the lens of the present invention, store the lens in such a state that a change in dimensions is suppressed, and the stored lens has excellent wetting properties and can be worn as such on the eye without necessitating rinse of the stored lens with purified water or the like.

BRIEF DESCRIPTION OF THE DRAWINGS

FIG. 3 is a graph showing the effect of an anionic monomer on drug release behavior.

DETAILED DESCRIPTION OF THE PREFERRED EMBODIMENTS

Figure 1:
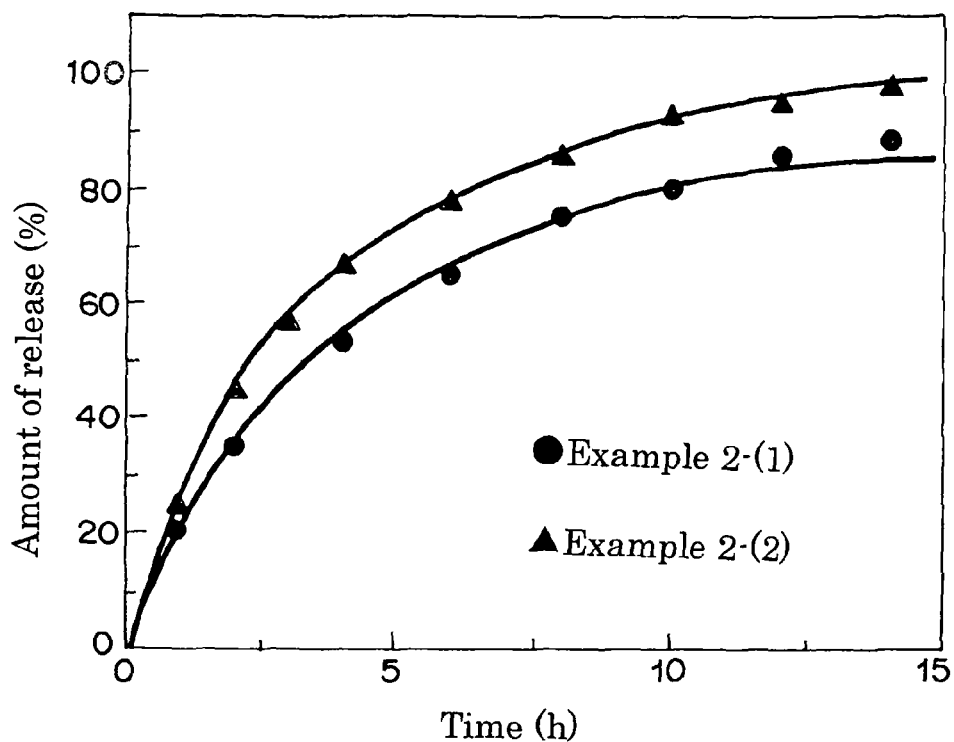
FIG. 1 is a graph showing the effect of an MAm-containing ophthalmic lens on sustained drug release.

The present invention is based on a finding obtained as a result of extensive study on various monomers having electrolyzable groups and polar groups.

That is, the present invention is based on the finding that a polymer gel having phosphate group-containing monomers of specific structure copolymerized therein has an excellent ability to include a cationic group-containing drug, suitable ionic properties, excellent transparency and form stability. The present invention is further based on the finding that by introducing, as a copolymer component, a monomer containing a nitrogen atom in its side chain, the nitrogen atom in the polymer interacts with a nitrogen atom in a cationic group-containing drug included therein, whereby the drug is efficiently supported and released. That is, the present invention provides a drug delivery ophthalmic lens which can effectively retain and sustainedly release a drug and is excellent in transparency, form stability and strength, because the polymer gel having a phosphate group and a nitrogen atom in its side chain can retain a cationic group-containing drug strongly by ionic bonding with the phosphate group, and can form a stabilized form of the included drug by relatively weak intermolecular interaction of the nitrogen atom in the polymer with a nitrogen atom in the drug molecule. The amount of the drug to be included is governed by stronger interaction generated in the polymer gel, so the drug can be included in an amount corresponding to the amount of phosphate groups introduced into the polymer gel.

Further, the present invention is based on the finding that the ophthalmic lens for including an anionic group-containing drug therein, prepared by copolymerizing a suitable amount of an anionic monomer with a cationic monomer, can include in the polymer gel the anionic group-containing drug in a proportion calculated in terms of a difference in content between the cationic monomer and the anionic monomer, with less change in shape before and after release of the drug.

The hydrophilic monomer in the present invention has at least one kind of hydrophilic group in its molecule. For example, the hydrophilic monomer having a hydroxyl group includes 2-hydroxymethyl (meth)acrylate, 2-hydroxyethyl (meth)acrylate, 2-hydroxypropyl (meth)acrylate, 2,3-dihydroxypropyl (meth)acrylate etc., and other hydrophilic monomers include, for example, 2-polyethylene glycol mono (meth)acrylate, 2-propylene glycol (meth)acrylate, N,N-dimethyl (meth)acrylamide, N,N-diethyl (meth)acrylamide, N-vinyl pyrrolidone etc., and these can also be used as a mixture of two or more thereof (In the present invention, "(meth)acrylate" means both acrylate and methacrylate.).

In the present invention, the monomer having a phosphate group retains a cationic drug strongly by interaction with the phosphate group in the copolymer, to exhibit an excellent effect of sustained release, and specific examples are methacrylates represented by the following structural formula (I). Among these, n is an integer of 1 to 4, particularly preferably 2. When n is 5 or more, an alkylene chain in the molecule is so long that the copolymer cannot sufficiently interacts with the drug, and the amount of the drug included or sustained released is influenced, and an excellent effect of sustained release cannot be achieved.

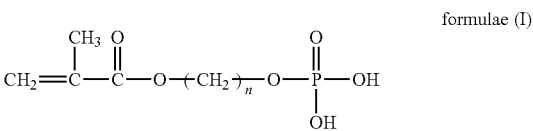

formulae (I)

n: 1~4

The amount of the phosphate group-containing monomer (formula (I)) used is preferably in the range of 0.1 to 40 wt %, particularly preferably in the range of 1 to 20 wt %, based on the hydrophilic monomer. When the amount of the phosphate group-containing monomer is less than 0.1 wt %, a sufficient amount of the drug included may be hardly obtained, while when the amount is higher than 40 wt %, the form stability and mechanical strength of the lens as polymer gel may be decreased.

The phosphate group-containing monomers of the following structural formulae (II) and (III), in addition to the formula (I) above, can also be used in the present invention. In this case, it is preferable that the total amount of the monomers of the structural formulae (II) and (III) is 0.5 to 20 wt % based on the amount of the monomers in total, and the amount of the compound of the structural formula (II) is 75 to 85 wt % based on the total amount of the monomers of the structural formulae (II) and (III).

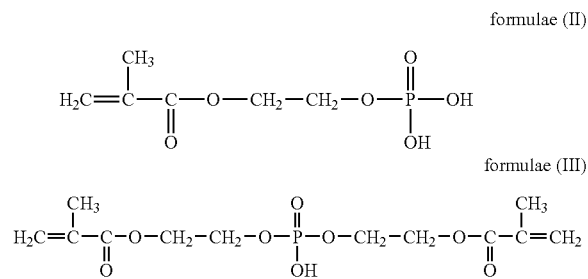

The monomer containing a nitrogen atom in its side chain used in the present invention is a monomer having one (meth) acryl group and in its end a nitrogen atom, and examples thereof include, but are not limited to, (meth)acrylamide, N,N-dimethyl (meth)acrylamide, N,N-diethylaminoethyl (meth) acrylate, N,N-dimethylaminopropyl (meth) acrylamide, and N,N-diethyl (meth)acrylamide. Among these exemplary compounds, methacrylamide is particularly preferable. The two or more of the exemplary compounds can be simultaneously used.

The amount of the monomer containing a nitrogen atom in its side chain is preferably in the range of 0.05 to 40 wt %. When the amount is less than 0.05 wt %, its influence on improvement on the power to include a drug is low, while when the amount is higher than 40 wt %, the interaction among nitrogen atoms in polymer chains occurs predominantly, and the interaction between the included drug and a nitrogen atom in a chain of the polymer is lowered, thus hardly attaining excellent controlled release. The amount of the drug included reaches a peak when the content of the monomer containing a nitrogen atom in its side chain is 15 wt %, and the tensile elongation as lens strength tends to be lowered when the content of the monomer containing a nitrogen atom in its side chain exceeds 30 wt %. Accordingly, the amount is particularly preferably 1 to 30 wt % in consideration of the amount of the drug included and the strength of the lens. That is, when the amount is in this range, the pharmacokinetics of the ophthalmic lens can be controlled to achieve practically usable lens strength.

In the present invention, a crosslinking monomer can be used in addition to the components described above. Although the crosslinking monomer may or may not be used, the formation of a network structure of the polymer gel and the mechanical strength of the gel can be controlled by using the crosslinking monomer. The crosslinking monomer includes, for example, ethylene glycol dimethacrylate, methylene bisacrylamide, 2-hydroxy-1,3-dimethacryloxy propane, trimethylol propane triacrylate, etc. The amount of the crosslinking monomer used is preferably 0.1 to 4.0 wt %, more preferably 0.1 to 1.0 wt %, based on the amount of the used monomers in total. When the amount of the crosslinking monomer is too low, an regulatory effect on form stability of the polymer gel is not observed. On the other hand, when the amount of the crosslinking monomer is too high, the network structure is in excess, and the polymer gel becomes brittle.

In the present invention, the monomer having a cationic group in its side chain is a monomer which in the copolymer, retains an anionic drug strongly by ionic interaction. Examples of such monomers include vinyl benzyl trialkyl ammonium salts (particularly ammonium chloride) such as vinyl benzyl dimethyl methyl ethyl ammonium salt, vinyl benzyl dimethyl n-butyl ammonium salt and vinyl benzyl triethyl ammonium, and ethyl methacrylate (particularly ammonium chloride) such as 2-methacryloxy ethyl trimethyl ammonium salt, 2-methcryloxy ethyl dimethyl ethyl ammonium salt and 2-methacryloxy ethyl dimethyl n-pentyl ammonium salt, and two or more of these compounds can be simultaneously used. For demonstrating the features of the present invention, the number of cationic and anionic groups should be strictly regulated, and for this purpose, the amount of the ionic monomers incorporated is calculated desirably in terms of mol %. In the present invention, the amount of the cationic monomer used is desirably smaller than the amount of the hydrophilic monomer, and specifically the amount of the cationic monomer is preferably in the range of 2 to 50 mol %, more preferably in the range of 5 to 20 mol %, relative to the hydrophilic monomer. When the amount of the cationic monomer is less than 2 mol %, the amount of the drug included in the polymer gel tends to be decreased. When the amount exceeds 50 mol %, the polymer gel has an increased water content and thus hardly maintains form stability and mechanical strength.

In the present invention, the monomer having an anionic group in its side chain exhibits an effect on form stability of the polymer gel before and after drug release because the anionic group exerts ionic interaction strongly on a cationic group in the copolymer. For example, when the ratio of the anionic group to the cationic group is 1:1, the ionic interaction in the copolymer acts strongly to make the polymer gel excellent in form stability. When the cationic group is in excess, an excess of the cationic group acts as a drug ligand to contribute to inclusion of the drug having an anionic group in its molecule. Under the physiological environment, the polymer gel having the drug included therein releases the included drug by ion-exchange reaction with chloride ions etc. present in the environment. The cationic group in the copolymer after release of the drug is rendered cationically charged, but undergoes ionic interaction with the anionic group in the copolymer, so the distance among molecules can be kept constant. Even if the cationic group in the copolymer is cationically charged after release of the drug, the polymer gel of the present invention does not generate ionic repulsion among molecules by this mechanism, and is thus excellent in form stability.

For example, the monomer having an anionic group in its side chain, which is necessary for exhibiting this mechanism, includes (meth)acrylic acid, (meth)acryloyloxy ethyl succinic acid, (meth)acryloyloxy ethyl phosphate, (meth)acryloyloxy methyl phosphate, (meth)acryloyloxy propyl phosphate etc., and two or more of these compounds can be used. The anionic monomer is used in the range of 30 to 90 mol %, preferably 40 to 80 mol %, relative to the cationic monomer. When the amount of the anionic monomer is higher than 90 mol %, the charge of the cationic group acting as a drug ligand in the polymer gel is cancelled, so the cationic group does not generate ionic interaction with the drug having an anionic group, thus failing to include the drug in the polymer gel. On the other hand, when the amount of the anionic monomer is less than 30 mol %, the action of the cationic group is high, so the influence thereof by interacting with the anionic group is decreased, and thus there is a significant change in shape of the polymer gel before and after release of the drug, to make the gel unstable.

As described above, the present invention is characterized by the amount of the cationic and anionic monomers incorporated. That is, the amount of the drug included can be regulated by the amount of the cationic monomer added. Depending on the solubility of the drug in water, the minimum effective concentration to exhibit efficacy, and the maximum concentration for safety, the amount of the cationic monomer can be determined suitably for individual drugs, and the monomer composition can be designed depending on the amount of the drug.

For the effective sustained release effect and excellent form stability characteristic of the present invention, the amount of the anionic monomer compounded should be in the range of 90 to 30 mol % relative to the cationic monomer. When the anionic monomer is added in an amount of 100 mol % relative to the cationic monomer, the drug is not included at all. This is due to the fact that because the amount of the cationic monomer is equal to the amount of the anionic monomer, the charge of the polymer gel is cancelled so that the gel cannot ionic-interact with the drug. When the amount of the anionic monomer added is less than 30 mol %, the shape of the polymer gel is significantly changed before and after release of the drug, to make it practically unusable. This is because the amount of the anionic monomer added is so small that the polymer gel cannot be influenced by interaction of the cationic group with the anionic group after drug release, and thus the repulsion among cation charges cannot be regulated, resulting in a significant change in shape before and after release.

When the cationic polymer gel of the present invention is used as a drug delivery sheet, the sheet is not released after drug release because of no or less change in shape. However, when the predetermined amount of the anionic monomer is not contained, the sheet is released because of change in shape after drug release. That is, a practical polymer gel sheet can be provided by suitably mixing the cationic monomer with the anionic monomer.

In the present invention, an arbitrary copolymerizable monomer can also be used. For example, a hydrophobic monomer can be used to achieve fine adjustment of the regulatory action on the water content and swelling degree of the resulting polymer gel and the amount of the drug included in the polymer gel. The hydrophobic monomer used is not limited insofar as it is compatible with the hydrophilic monomer, the phosphate group-containing monomer and the anionic and cationic monomers used in the present invention, and preferable examples include methyl (meth)acrylate, isobutyl (meth)acrylate, 2,2,2-trifluoro(meth)acrylate, cyclohexyl (meth)acrylate etc. Hydrophilic monomers other than the hydrophilic monomer having a hydroxyl group in its molecule and the monomer containing a nitrogen atom in its side chain can also be used.

The drug having a cationic group which can be used in the drug delivery ophthalmic lens of the present invention is an organic compound having, in its molecular structure, at least one kind of substituent such as a quaternary ammonium base and a primary to tertiary ammonium base. The drug exhibiting a preferable pharmacological effect includes, for example, neostigmine methylsulfate, oxybuprocaine hydrochloride, naphazoline nitrate, naphazoline hydrochloride, sodium chondroitin sulfate, pilocarpine hydrochloride, distigmine bromide, ecothiopate iodine, epinephrine, epinephrine hydrogen tartrate, carteolol hydrochloride, befunolol hydrochloride, ketotifen fumarate, acyclovir, lysozyme chloride, tobramicin, latanoprost, isoprolyl unoprostone ester, etc.

The drug having an anionic group which can be used in the drug delivery polymer gel of the present invention is an organic compound having, in its molecular structure, at least one kind of anionic group such as a sulfo group, carboxyl group and phosphate group. The drug which can be used in the ophthalmic field includes, for example, sodium guaiazulene sulfonate, sodium cromoglicate, dipotassium glycyrrhizinate, sodium prednisolone phosphate, sodium sulbenicillin, sodium dexamethasone phosphate, sodium betamethasone phosphate, sodium pantothenate, sodium flavin adenine nucleotide, sodium diclofenac, sodium hyaluronate, sodium chondroitin sulfate, sodium ecabet, etc.

The polymer gel having sustained drug releasability according to, the present invention can be used in various applications. The drug delivery system (DDS) includes sterilized sheets, antibacterial sheets, wound-covering materials, compress materials etc., and the drug to be used can be selected suitably depending on applications.

In production of the ophthalmic lens of the present invention, a polymerization initiator is added to, and dissolved in, a mixture of the monomers under stirring. As the polymerization initiator, a general radical polymerization initiator for example a peroxide such as lauroyl peroxide, cumene hydroperoxide or benzoyl peroxide, or azobisvaleronitrile, azobisisobutyronitrile (AIBN) or the like can be used. The amount of the polymerization initiator added is preferably about 10 to 3500 ppm based on the total amount of the monomers.

The monomer mixture is introduced into a metallic, glass, or plastic mold for ophthalmic lens, which is then closed and heated stepwise or continuously in the range of 25 to 120° C. in e.g. a thermostatic bath, and the polymerization is completed in 5 to 120 hours. In polymerization, UV rays, electron rays, gamma rays etc. can also be used. Solution polymerization can also be applied by adding water or an organic solvent to the monomer mixture.

After the polymerization is finished, the polymerization mixture is cooled to room temperature, and the resulting polymer is removed from the mold, cut and polished as necessary. The resulting ophthalmic lens is swollen by hydration to form a hydrous gel. A liquid (swelling solution) used in swelling by hydration includes, for example, water, physiological saline, an isotonic buffer solution etc. The swelling solution is heated to 60 to 100° C., and the ophthalmic lens is immersed therein for a predetermined time, whereby it is rapidly swollen by hydration. By this swelling treatment, it is also made possible to remove unreacted monomers contained in the polymer.

Then, the procedures of including the drug in the present invention are described. A drug having ionic properties selected depending on applications is dissolved to prepare a drug solution, and the hydrous gel described above is immersed in the drug solution, to form a drug delivery ophthalmic lens having the drug included in the hydrous gel.

The solvent in which the drug is to be dissolved includes water, a hydrophilic solvent, a mixed solvent of water and a hydrophilic solvent, and the hydrophilic solvent includes, for example, alcohols such as ethanol, methanol, isopropanol and n-butanol, dimethyl sulfoxide, etc.

The concentration of the drug contained in the drug solution is selected suitably depending on the solubility of the drug, the minimum effective concentration for exhibiting efficacy and the maximum concentration for safety, but is generally preferably in the range of $1.0 \times 10^{-6}$ to $10^{-2}$ mol/L.

A solution which contains a nonionic surfactant and a nonionic osmotic pressure regulating agent but does not contain an ionic compound is used as the lens storing solution of the present invention. The nonionic surfactant referred to in the present invention forms a layer of the surfactant on the surface of SCL, to exert an effect of preventing the included drug from being eluted. The nonionic surfactant can also confer hydrophilicity on the surface of SCL, thus improving the wetting properties of the lens after dipping, to make feel upon wearing excellent. The nonionic surfactant includes, for example, surfactants based on polyoxyethylene ether, polyoxypropylene ether, or a polyoxyethylene/polyoxypropylene block copolymer, among which a polyoxyethylene/polyoxypropylene block copolymer-based polymer is preferable.

The nonionic surfactant used preferably in the present invention is based on a block polymer (poloxamer type) having ethylene oxide added to both ends of polypropylene glycol, wherein the content of ethylene oxide in the molecule is preferably 60 to 80 wt %, and the molecular weight is preferably 4000 or more. When the content of ethylene oxide is lower than 60 wt %, the aqueous solution is easily made turbid and is not practical. When the molecular weight is too low, the surfactant enters a network structure of SCL material as hydrogel, to facilitate elution of the drug, or causes a reduction in safety of the lens itself and a change in dimension undesirably.

Generally, HLB value (hydrophile-lipophile balance) is used as an indicator of relative balance between hydrophilicity and lipophilicity of a surfactant. A nonionic surfactant of polyoxyethylene/polyoxypropylene having an HLB value of 12 to 16 is used in the present invention. When the HLB value is smaller than 12, the surfactant cannot confer sufficient hydrophilicity, has lower affinity for the surface of SCL, and cannot achieve a sufficient effect for preventing reduction in wetting properties and elution of the drug. When the HLB value is greater than 16, water molecules around SCL interact with the surfactant and enter the gel, resulting in failure to give a lens having stable dimensions.

The nonionic surfactant (poloxamer type) used in the present invention may be any of nonionic surfactants satisfying the above conditions, and specific examples include Lutrol F108, F98, F88, F68 and F38 having an ethylene oxide content of 80% in the molecule and Lutrol F127 and F77 having an ethylene oxide content of 70% in the molecule among Pluronic® series manufactured by Asahi Denka Kogyo K.K.

Because the drug delivery SCL has the drug included in the lens, washing with purified water or the like prior to use in the eyes is not preferable. Accordingly, the nonionic surfactant and the osmotic pressure regulating agent in the storing solution should be added in such an amount that while the eyes are not irritated, the drug in the lens is not eluted.

For example, the amount of the nonionic surfactant added is generally preferably 0.005 to 1.0 wt %, more preferably 0.01 to 0.5 wt %. When the amount of the nonionic surfactant is lower than 0.005 wt %, the effect of the nonionic surfactant added cannot be sufficiently demonstrated, and the wetting properties of the surface of SCL are lowered, thus failing to achieve excellent feel upon wearing. Because a layer of the nonionic surfactant is not formed on the surface of SCL, its inhibitory effect on elution of the drug included in the polymer gel cannot be expected. An amount of greater than 1.0 wt % is not preferable either because the eyes are irritated by the surfactant.

When SCL comprising a hydrogel is immersed in purified water or a storing solution having significantly different osmotic pressure from that of the hydrogel, the dimensions of the gel are changed due to a difference in osmotic pressure between the inside and the outside of the gel. Hence, the osmotic pressure of the storing solution should be regulated to the same level as in tears, and for this purpose, an ionic osmotic pressure regulating agent such as potassium chloride or sodium chloride is generally used. For the drug delivery SCL utilizing ion-exchange reaction, however, a storing solution using the ionic osmotic pressure regulating agent is problematic because the drug included in the gel is eluted.

Accordingly, the ionic compound cannot be used in the storing solution of the present invention, and a nonionic compound is used to regulate the osmotic pressure of the storing solution in the range of 200 to 400 mmol/kg, preferably in the range of 220 to 380 mmol/kg, substantially equal to the physiological osmotic pressure. When the osmotic pressure is lower than 200 mmol/kg, the osmotic pressure of SCL immersed in the storing solution becomes lower than in tears. Accordingly, tears enter SCL to increase the dimensions of the lens, to allow it to adhere to the eyeball. When the osmotic pressure is higher than 400 mmol/kg, the osmotic pressure regulating agent in the lens is rapidly discharged to decrease the dimensions of the lens to cause pain upon wearing.

As the nonionic osmotic pressure regulating agent in the present invention, one member selected from glycerin, ethylene glycol, propylene glycol, polyethylene glycol, glucose, fructose, mannitol, sorbitol, xylitol, cyclodextrin and trehalose, or a suitable mixture thereof, can be incorporated into the storing solution.

In the present invention, various thickeners showing nonionic properties in solution, for example, arbitrary components such as methyl cellulose, hydroxyethyl cellulose, hydroxypropyl cellulose, polyethylene oxide, polyvinyl alcohol, and polyvinyl pyrrolidone can be added. Components showing ionic properties in solution, such as a preservative, a bactericidal agent, an antibacterial agent and a buffering agent, for example cationic polymers such as polyhexamethylene biguanide (PHMB) can also be added as arbitrary components in an amount of e.g. 2 ppm or thereabout in which the functions of the drug delivery SCL used in the present invention are not affected.

The storing solution of the present invention can be easily obtained by dissolving the predetermined amounts of the nonionic surfactant and the nonionic osmotic pressure regulating agent in purified water under stirring at room temperature. With respect to the sterilization method, the resulting storing solution may be sterilized by filtration, heating/pressurization, or irradiation with electron rays. When this storing solution is used, SCL having the drug included therein may be immersed in this solution and sterilized in a sealed state for distribution in a hygienic state.

Hereinafter, the present invention is described in detail by reference to the Examples, but the present invention is not limited to these examples.

Example 1

According to the following method, the effective amount of methacrylamide (MAm) added was confirmed from the amount of a drug included and tensile elongation.

MAm was added to a concentration of 0%, 0.05%, 0.1%, 1%, 15%, 30%, or 40% to a mixture consisting of 94.8 wt % 2-hydroxyethyl methacrylate (HEMA), 5 wt % methacryloxyethyl phosphate (structural formula (I): m=2) (MOEP), 0.2 wt % ethylene glycol dimethacrylate (EDMA), and 2000 ppm AIBN, and each mixture was stirred for about 1 hour in a nitrogen atmosphere. The mixture to which 0% MAm was added was a comparative example. After stirring, each monomer mixture was introduced into a mold for ophthalmic lens and heated over 25 hours to a temperature in the range of 50 to 100° C. to give a polymer. The resulting polymer was returned to room temperature, then removed from the mold and immersed in distilled water at about 80° C. for about 4 hours, whereby it was swollen by hydration. Any ophthalmic lens thus obtained was a colorless transparent hydrous gel having a water content of 43%. Each polymer gel was immersed for 48 hours in 10 mL of 0.5 wt % aqueous solution of naphazoline nitrate at 25° C. prepared previously as a model drug, whereby the naphazoline nitrate was included therein. The ophthalmic lens having the naphazoline nitrate included therein was immersed in 20 ml distilled water at 25° C. for 24 hours, to remove the free drug not ionic-interacting with a phosphate group.

The ophthalmic lens having the naphazoline nitrate included therein was immersed in 10 ml physiological saline at 25° C., and the immersion solution was sampled with time for 24 hours, and the amount of naphazoline nitrate contained in the immersion solution was quantified by HPLC (JASCO Corporation). This quantification was repeatedly carried out until release of the drug into the immersion solution could not be completely confirmed, and the degree of the drug included in the ophthalmic lens was calculated from the total amount of the drug eluted into the immersion solution. In a tensile test, the lens was cut into a rectangular strip of 2×10 mm, which was then measured by a tensile testing machine. The results are shown in Table 1.

Example 2

By the following method, the behavior of inclusion of a drug was confirmed.

HEMA, MOEP (structural formula (I): m=2), MAm, EDMA, and 2000 ppm AIBN were mixed in a proportion shown in Table 2, and each mixture was stirred for about 1 hour in a nitrogen atmosphere, and from each mixture, an ophthalmic lens was obtained in the same manner as in Example 1. According to Example 1, naphazoline nitrate was included as a drug model in the resulting ophthalmic lens. According to Example 1, the amount of the drug included therein was quantified. Example 2-(2) was a comparative example.

The sustained drug release curves are shown in FIG. 1. The result indicated that the release rate of the MAm-containing ophthalmic lens in Example 2-(1) was lower than in Example 2-(2). That is, it can be confirmed that excellent drug retention performance and highly efficient sustained drug release performance can be achieved by incorporating nitrogen atoms into the ophthalmic lens.

Figure 2:
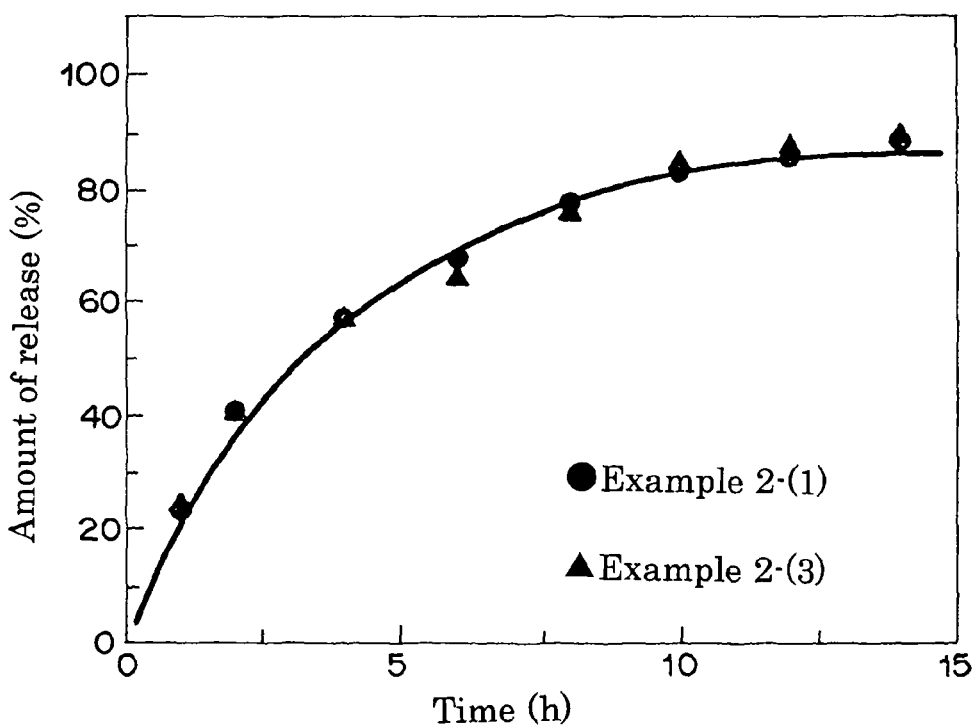
FIG. 2 is a graph showing the relationship between sustained drug releasability and a chemical structure.

The ophthalmic lens using no crosslinking monomer in Example 2-(3) and the drug delivery ophthalmic lens in Example 2-(1) indicated the same behavior of sustained release. These sustained drug release curves are shown in FIG. 2. That is, it can be confirmed that the sustained drug releasability according to the present invention is influenced significantly by ion-exchange reaction with phosphate groups and interaction among nitrogen atoms, rather than by regulation of the drug by a network structure formed by the crosslinking component.

Example 3

Measurement results of the size of each ophthalmic lens in physiological saline before and after drug release in Examples 2-(1), (2), (3) are shown in Table 2. It was recognized that like the ophthalmic lens in Example 2-(1), the ophthalmic lens in Example 2-(3) was excellent in form stability with less change in size, while the MAm-free lens in Example 2-(2) showed a significant change in size. That is, it can be confirmed that the drug delivery ophthalmic lens of the present invention is excellent in form stability even if it does not contain a crosslinking monomer.

TABLE 1

| Example 1 | MAm (wt %) | Amount of drug included ($\times 10^{-5}$ mol) | Tensile elongation (%) |
|---|---|---|---|
| (1) | 0 | 7.29 | 230 |
| (2) | 0.05 | 7.42 | 230 |
| (3) | 0.10 | 7.41 | 250 |
| (4) | 1.00 | 8.30 | 260 |
| (5) | 15.0 | 9.80 | 265 |
| (6) | 30.0 | 9.36 | 270 |
| (7) | 40.0 | 8.20 | 255 |

TABLE 2

| Example 2 | HEMA (wt %) | MOEP (wt %) | MAm (wt %) | EDMA (wt %) | Before release (mm) | After release (mm) |
|---|---|---|---|---|---|---|
| (1) | 84.8 | 5 | 10 | 0.2 | 14.0 | 14.0 |
| (2) | 94.8 | 5 | 0 | 0.2 | 14.0 | 14.5 |
| (3) | 85.0 | 5 | 10 | 0 | 14.0 | 14.1 |

Example 4

Methacrylamide propyl trimethyl ammonium chloride (MAPTAC) was added in a proportion shown in Table 3 to 1 mol of 2-hydroxyethyl methacrylate (HEMA), then 2-methacryloyloxyethyl phosphate (MOEP) in an amount of 50 mol % relative to MAPTAC was mixed with each mixture, 3000 ppm ethylene glycol dimethacrylate (EDMA) (external) and 3000 ppm azobisisobutyronitrile (external) were added thereto, and each mixture was stirred for about 1 hour in a nitrogen atmosphere. After stirring, each monomer mixture was introduced into a mold for ophthalmic lens and heated over 25 hours to a temperature in the range of 50 to 100° C. to give a polymer. The resulting polymer was returned to room temperature, then removed from the mold and immersed in distilled water at about 80° C. for about 4 hours, whereby it was swollen by hydration. This polymer gel was immersed for 48 hours in 10 ml of 0.5 wt % aqueous solution of sodium guaiazulene sulfonate (water-soluble azulene) prepared previously as a model drug, whereby the water-soluble azulene was included therein. The ophthalmic lens having the water-soluble azulene included therein was immersed in 20 ml distilled water at 25° C. for 24 hours, to remove the free water-soluble azulene not ionic-interacting with MAPTAC. The ophthalmic lens having the water-soluble azulene included therein was immersed in 10 ml physiological saline at 25° C., and the immersion solution was sampled with time for 24 hours, and the water-soluble azulene contained in the immersion solution was quantified by HPLC. This quantification was repeatedly carried out until release of the drug into the immersion solution could not be completely confirmed, and the degree of inclusion of the drug in the ophthalmic lens was calculated from the total amount of the drug eluted into the immersion solution.

From the amount of the monomers compounded and the total amount of the drug eluted into the immersion solution determined by high performances liquid chromatography (HPLC, JASCO Corporation), the degree of inclusion of the drug was calculated according to the following equation:

Degree of inclusion of drug (%)=amount of drug included (mol)/(amount of cationic monomer compounded (mol)−amount of anioni monomer compounded (mol))×100

The form stability of the ophthalmic lens was evaluated by measuring the lens before and after drug release by a contact-lens projector. ⊚ was given when the shape was good, and x was given when warpage or deformation was recognized.

The results are shown in Table 3.

Example 5

10 mol % MAPTAC was mixed with 1 mol HEMA, and MOEP was mixed in a proportion shown in Table 4 with 10 mol % MAPTAC, then 3000 ppm EDMA (external) and 3000 ppm AIBN (external) were added thereto, and each mixture was stirred for about 1 hour in a nitrogen atmosphere. Examples 5-(1), (5), (6) were comparative examples. After stirring, the mixture was polymerized and swollen by hydration in the same manner as in Example 4. Water-soluble azulene was included in the resulting ophthalmic lens in the same manner as in Example 4. After free water-soluble azulene was removed, the amount of the water-soluble azulene released from the ophthalmic lens to physiological saline was quantified in the same manner as in Example 4 to calculate the amount of the drug included in the lens. The results are shown in Table 4. It can be confirmed that when the amount of the anionic monomer MOEP is in the range of 30 to 90 mol % relative to the cationic monomer MAPTAC, each ophthalmic lens is excellent in form stability while maintaining a higher degree of inclusion of the drug. The behaviors of elution of the drug in Example 5-(3) using a suitable amount of the anionic monomer and in Example 5-(6) not using the anionic monomer are shown in FIG. 3. The effect of the anionic monomer incorporated can be confirmed from the sustained drug release curves in FIG. 3.

Example 6

For reference, a sheet was used for evaluate the anionic monomer incorporated. The monomers mixed at the same proportion as in Example 5-(3) or Example 5-(6) were applied onto a transparent plastic sheet and cured by irradiation with UV rays. The resulting film was swollen by hydration and allowed to include the drug in the same manner as in Example 4. Further, the included drug was released in the same manner as in Example 4. The evaluation results that ⊚ was given when the film was excellent in adhesion to the transparent plastic sheet before and after drug release, and x was given when the film was released are shown in Table 7. The effect of the incorporated anionic monomer on form stability can thereby be confirmed.

TABLE 4

| Example 5 | MOEP (mol %) | Shape | Size (mm) before release/after release | | Water content (%) | Water content (%) |
|---|---|---|---|---|---|---|
| (1) | 100 | ⊙ | 13.2 | 13.2 | 55 | 0 |
| (2) | 90 | ⊙ | 13.2 | 13.2 | 55 | 95 |
| (3) | 60 | ⊙ | 13.6 | 13.6 | 55 | 96 |
| (4) | 30 | ⊙ | 13.8 | 13.9 | 58 | 95 |
| (5) | 20 | x | Shape is not stabilized | | 70 | 97 |
| (6) | 0 | x | Shape is not stabilized | | 76 | 95 |

Water content (%) = (weight of water contained − dry weight)/(dry weight) × 100

TABLE 5

| | Before release | After release |
|---|---|---|
| Example 5-(3) | ⊙ | ⊙ |
| Example 5-(6) | ⊙ | x (release) |

(Method of Evaluation of a Storing Solution)

The drug delivery SCL having a cationic or anionic ligand obtained above was immersed in a storing solution, and the amounts of the drug eluted from the lens to the storing solution just after sterilization and 30 days after storage were quantified by using high performance liquid chromatography (HPLC, JASCO Corporation).

When the amount of the drug eluted was 0 to less than 1 ppm, ○ was given, and when the amount was 1 ppm or more, the lens was not practical, so x was given.

Example 7

In this example, the elution of the drug from the lenses produced in Examples 1 to 4 into a storing solution was confirmed. Naphazoline nitrate was used as the drug having a cationic group, and water-soluble azulene was used as the drug having an anionic group. The ionic properties of lenses (I), (II), (III) and (IV), specific constituent components thereof, and amounts of the components incorporated are shown in Table 6.

4.0 g propylene glycol and 0.1 g nonionic surfactant Lutrol F127 were added to purified water, dissolved at room temperature under stirring, and adjusted with purified water to a volume of 100 mL and regulated such that the pH became 5.0 to 7.5 and the osmotic pressure became 220 to 380 mmol/kg. The resulting solution, 5.0 mL, was introduced into a glass vial, then each of the drug delivery SCLs (I) to (IV) was introduced into it, sealed, and sterilized at 121° C. for 20 minutes, and the amount of the drug eluted was quantified according to the evaluation method described above.

TABLE 3

| Example 4 | MAPTAC (mol %) | MOEP (mol %) | Shape | Size (mm) before release/after release | | Water content (%) | Degree of inclusion of drug (%) |
|---|---|---|---|---|---|---|---|
| (1) | 2 | 50 | ⊙ | 13.7 | 13.7 | 48 | 95 |
| (2) | 5 | 50 | ⊙ | 13.6 | 13.6 | 50 | 98 |
| (3) | 10 | 50 | ⊙ | 13.5 | 13.5 | 55 | 98 |
| (4) | 20 | 50 | ⊙ | 13.2 | 13.3 | 58 | 95 |
| (5) | 50 | 50 | ⊙ | 13.0 | 13.1 | 63 | 97 |

Water content (%) = (weight of water contained − dry weight)/(dry weight) × 100
MOEP (mol %): Its amount is expressed relative to MAPTAC.

Elution was hardly observed both just after sterilization and after 30 days. The evaluation results after 30 days are shown in Table 7.

Examples 8 to 17

The formulations shown in Table 7 below were evaluated in the same manner as in Example 7. Like Example 7, elution was hardly observed both just after sterilization and after 30 days. The evaluation results after 30 days are shown in Table 7.

Comparative Example 1

In the same operation as in Example 1, osmotic pressure was regulated at about 220 to 380 mmol/kg by sodium chloride and potassium chloride as an ionic osmotic pressure regulating agent in place of the nonionic osmotic pressure regulating agent, and each lens was evaluated in the same manner as in Example 1. The amount of the drug eluted from any of the lenses (I) to (IV) was 1000 ppm or more just after sterilization and after 30 days, indicating that the lenses were not suitable for practical use. The evaluation results after 30 days are shown in Table 7.

TABLE 6

| Class | Type of SCL | HEMA | MOEP | MAPTAC | MAm | ED | AIBN (ppm) |
|---|---|---|---|---|---|---|---|
| (I) | Anionic SCL | 84.8 | 5.0 | | 10.0 | 0.2 | 2000 |
| (II) | Anionic SCL | 94.8 | 5.0 | | | 0.2 | 2000 |
| (III) | Cationic SCL | 93.0 | 2.3 | 4.7 | | 0.2 | 2000 |
| (IV) | Cationic SCL | 87.0 | 4.3 | 8.7 | | 0.2 | 2000 |

Unit of monomer amount: anionic SCL, wt %; cationic SCL, mol %
HEMA: 2-hydroxyethyl methacrylate
MOEP: methacryloxyethyl phosphate
MAPTAC: methacrylamide propyl trimethyl ammonium chloride
MAm: methacrylamide
ED: ethylene glycol dimethacrylate

TABLE 7

| | Amount of osmotic pressure regulating agent (wt %) | Amount of surfactant (wt %) | Evaluation results of drug elution from each type after 30 days (ppm) | | | |
|---|---|---|---|---|---|---|
| | | | Lens (I) | Lens (II) | Lens (III) | Lens (IV) |
| Example 1 | PG(4.0) | F127(0.1) | ○ | ○ | ○ | ○ |
| Example 2 | PG(4.0) | F127(0.5) | ○ | ○ | ○ | ○ |
| Example 3 | PG(4.0) | F127(0.05) | ○ | ○ | ○ | ○ |
| Example 4 | PG(4.0) | F127(0.01) | ○ | ○ | ○ | ○ |
| Example 5 | PG(4.0) | F108(0.1) | ○ | ○ | ○ | ○ |
| Example 6 | PG(4.0) | F68(0.1) | ○ | ○ | ○ | ○ |
| Example 7 | PG(4.0) | F38(0.1) | ○ | ○ | ○ | ○ |
| Example 8 | PG(4.5) | F127(0.1) | ○ | ○ | ○ | ○ |
| Example 9 | PG(3.5) | F127(0.1) | ○ | ○ | ○ | ○ |
| Example 10 | PG(2.5) | F127(0.1) | ○ | ○ | ○ | ○ |
| Example 11 | Glycerol (4.0) | F127(0.1) | ○ | ○ | ○ | ○ |
| Comparative Example 1 | NaCl + KCl | F127(0.1) | x | x | x | x |

INDUSTRIAL APPLICABILITY

According to the present invention, there can be obtained a drug delivery lens excellent in strength with less change in size and capable of efficiently including and sustainedly releasing a drug by utilizing ion-exchange reaction and intermolecular interaction.

Further, the storing solution of the present invention can, without eluting a drug included in the lens of the present invention, store the lens in such a state that a change in dimensions is suppressed, and the stored lens has excellent wetting properties and can be worn as such on the eye without necessitating rinse of the stored lens with purified water or the like.

The invention claimed is:

1. A drug delivery ophthalmic lens comprising a cationic group-containing drug in the inside of a copolymer, wherein the copolymer consists of:
   (a) a hydrophilic monomer having a hydroxyl group in its molecule;
   (b) at least one phosphate group-containing methacrylate represented by the following structural formula (I),

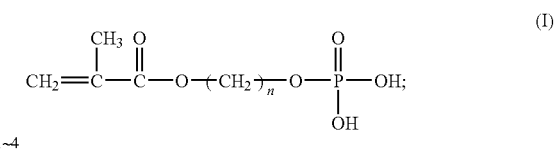

n: 1~4

(c) a monomer having a nitrogen atom in its side chain; and
   (d) a monomer copolymerizable with (a), (b) and (c),
   wherein a mixture of the following structural formulae (II) and (III) is used as the phosphate group-containing methacrylates:

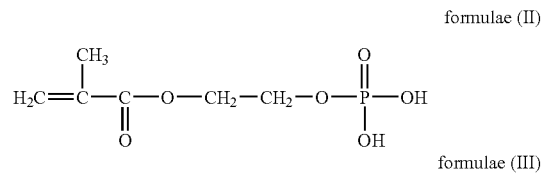

wherein the monomer having a nitrogen atom in its side chain is (meth)acrylamide and the copolymer contains anionic monomers in a ratio of 30 mol % to 90 mol % to the cationic monomer.

2. The drug delivery ophthalmic lens according to claim 1, wherein the content of the monomer having a nitrogen atom in its side chain is 0.05 to 40 wt %.

3. The drug delivery ophthalmic lens according to claim 1, wherein the cationic group-containing drug is an organic compound having at least one quaternary ammonium base or primary to tertiary amine base in its molecule.

4. A drug delivery ophthalmic lens comprising an anionic group-containing drug in the inside of a copolymer consisting of a hydrophilic monomer, cationic and anionic monomers, and a monomer copolymerizable with these components, wherein the copolymer contains the anionic monomer in a ratio of 30 to 90 mol % to the cationic monomer, wherein the anionic group-containing drug is an organic compound having at least one member selected from a carboxyl group, a sulfo group and a phosphate group in its molecule.

5. The drug delivery ophthalmic lens of claim 4, wherein the copolymer contains the anionic monomer in a ratio of 40 to 80 mol % to the cationic monomer.

6. The drug delivery ophthalmic lens of claim 5, wherein the anionic group-containing drug is water-soluble azulene.

7. The drug delivery ophthalmic lens according to claim 2, wherein the cationic group-containing drug is an organic compound having at least one quaternary ammonium base or primary to tertiary amine base in its molecule.

8. The drug delivery ophthalmic lens according to claim 2, wherein the total amount of the monomers of structural formulae (II) and (III) is 0.5 to 20 wt. % based on the amount of monomers in total, and the amount of the compound of the structural formula (II) is 75 to 85 wt. % based on the total amount of the monomers of the structural formulae (II) and (III).

9. The drug delivery ophthalmic lens according to claim 8, wherein the cationic group-containing drug is naphazoline nitrate.

* * * * *